US012773208B2

(12) United States Patent
Lee

(10) Patent No.: US 12,773,208 B2
(45) Date of Patent: Oct. 27, 2026

(54) UNIDIRECTIONAL AND BIDIRECTIONAL ANCHOR SCAFFOLDS

(71) Applicant: Bioforma, Inc., Winnetka, IL (US)

(72) Inventor: Michael J. Lee, Winnetka, IL (US)

(73) Assignee: Bioforma, Inc., Winnetka, IL (US)

( * ) Notice: Subject to any disclaimer, the term of this patent is extended or adjusted under 35 U.S.C. 154(b) by 1060 days.

(21) Appl. No.: 17/995,363

(22) PCT Filed: Aug. 18, 2021

(86) PCT No.: PCT/US2021/046517

§ 371 (c)(1),
(2) Date: Oct. 3, 2022

(87) PCT Pub. No.: WO2022/040323

PCT Pub. Date: Feb. 24, 2022

(65) Prior Publication Data

US 2023/0157690 A1 May 25, 2023

Related U.S. Application Data

(60) Provisional application No. 63/067,707, filed on Aug. 19, 2020.

(51) Int. Cl.

| | |
|---|---|
| ***A61B 17/064*** | (2006.01) |
| ***A61B 17/072*** | (2006.01) |
| ***A61F 2/00*** | (2006.01) |

(52) U.S. Cl.

CPC .... *A61B 17/07207* (2013.01); *A61B 17/0644* (2013.01); *A61F 2210/0004* (2013.01); *A61F 2220/0016* (2013.01)

(58) Field of Classification Search

CPC ........... A61F 2220/0016; A61F 2/0063; A61B 2017/081; A61B 2017/1103;

(Continued)

(56) References Cited

U.S. PATENT DOCUMENTS

2001/0044637 A1 11/2001 Jacobs et al.
2002/0077661 A1* 6/2002 Saadat ...................... A61F 2/08 606/221

(Continued)

FOREIGN PATENT DOCUMENTS

WO WO 2001/056477 A2 8/2001

OTHER PUBLICATIONS

Extended European Search Report in European Appln No. 21859067.7, dated Mar. 13, 2024, 7 pages.

(Continued)

*Primary Examiner* — Majid Jamialahmadi
(74) *Attorney, Agent, or Firm* — Fish & Richardson P.C.

(57) ABSTRACT

A wound closure device includes multiple base elements arranged in a repeating pattern and a first anchor extending from a first side of each base element of the multiple base elements in a first direction for securing itself to a first layer of tissue along a wound within a body. The wound closure device further includes a second anchor extending from a second side of each base element of the multiple base elements in a second direction that is opposite to the first direction for securing itself within a second layer of tissue along the wound, such that the wound closure device is configured to hold the first and second layers of tissue against each other to close the wound.

31 Claims, 4 Drawing Sheets

(58) Field of Classification Search
CPC ... A61B 17/0644; A61B 17/064; A61B 17/08; A61B 2017/0641; A61B 17/07207
See application file for complete search history.

(56) References Cited

U.S. PATENT DOCUMENTS

| | | | |
|---|---|---|---|
| 2006/0235447 | A1 | 10/2006 | Walshe |
| 2011/0288583 | A1 | 11/2011 | Goraltchouk et al. |
| 2018/0071071 | A1 | 3/2018 | Greenhalgh et al. |
| 2020/0214825 | A1 | 7/2020 | Gassler et al. |

OTHER PUBLICATIONS

International Preliminary Report on Patentability in International Appln. No. PCT/US2021/046517, mailed on Mar. 2, 2023, 8 pages.
International Search Report and Written Opinion in International Appln. No. PCT/US2021/046517, mailed on Nov. 9, 2021, 9 pages.

* cited by examiner

UNIDIRECTIONAL AND BIDIRECTIONAL ANCHOR SCAFFOLDS

CROSS-REFERENCE TO RELATED APPLICATIONS

This application is the national stage entry of International Patent Application No. PCT/US2021/046517, filed on Aug. 18, 2021, and claims priority to U.S. Provisional Patent Application No. 63/067,707, filed Aug. 18, 2020, the disclosures of which are incorporated herein by reference.

TECHNICAL FIELD

This disclosure relates to wound closure devices, such as scaffolds, and related methods of closing a wound.

BACKGROUND

The specific techniques and material employed to effect wound closure following surgical procedures (e.g., reconstructive plastic surgery) can have substantial effects on the long-term results of the procedure. This is particularly true where a large plane of separation between adjacent tissues (e.g., between a skin flap and underlying muscle/fascia) exists. Poor transmission of forces between the layers of tissue and/or parallel to the plane of the separation can result in dehiscence, seroma formation, hematoma, infection, tissue puckering or other negative cosmetic or functional effects, or other unwanted outcomes.

SUMMARY

An aspect of the present disclosure relates to a wound closure device for enhanced healing and tissue support including: (i) a flexible substrate; (ii) multiple base elements coupled to the flexible substrate at multiple locations across the flexible substrate; and (iii) multiple anchors, wherein each base element of the multiple base elements has coupled thereto at least one anchor of the multiple anchors, and wherein each anchor of the multiple anchors is configured to penetrate and fix itself within tissue, thereby anchoring the base elements to the tissue. The use of multiple anchors to couple the flexible substrate to tissue creates multidimensional fixation which improves surgical outcomes (e.g., improved cosmesis, reduced puckering, reduced seroma formation, reduced need for subsequent revision or other follow-up procedures) and reduces intra-surgical time and expertise (e.g., relative to placement of many individual sutures to provide fixation from one plane of tissue to another across a separated tissue interface) for a variety of procedures (e.g., mastectomy, diastasis recti repair) that require or otherwise include separation of tissue in multiple planes.

Another aspect of the present disclosure relates to a wound closure device for enhanced tissue anchoring including: an anchor, wherein the anchor is configured to penetrate and fix itself within tissue, and wherein the anchor includes a set of barbs directed outward from a center of the anchor and away from a tip of the anchor such that penetration of the anchor into tissue causes deformation of the barbs toward the center of the anchor and further such that retraction of the anchor subsequent to penetration of the anchor into the tissue causes the barbs to expand outward from the center of the anchor, thereby anchoring the anchor in the tissue. Such a deformable barb mechanism provides fixation that is superior to barbs of previously available surgical fixation devices.

Another aspect of the present disclosure relates to a method for forming an anchor of a wound closure device, the method including: (i) forming a shaft of the anchor, wherein the shaft terminates in a sharp point capable of penetrating tissue; and (ii) cutting two or more volumes of material from the shaft of the anchor, thereby forming two or more barbs that are directed outward from the shaft and away from the sharp point of the anchor such that penetration of the sharp point of the anchor into tissue causes deformation of the barbs toward the center of the shaft and further such that retraction of the anchor subsequent to penetration of the sharp point of the anchor into the tissue causes the barbs to expand outward from the shaft, thereby anchoring the anchor in the tissue.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

In another aspect, a wound closure device includes multiple base elements arranged in a repeating pattern and a first anchor extending from a first side of each base element of the multiple base elements in a first direction for securing itself to a first layer of tissue along a wound within a body. The wound closure device further includes a second anchor extending from a second side of each base element of the multiple base elements in a second direction that is opposite to the first direction for securing itself within a second layer of tissue along the wound, such that the wound closure device is configured to hold the first and second layers of tissue against each other to close the wound.

Embodiments may provide one or more of the following features.

In some embodiments, the wound closure device is configured to be disposed internal to the body between the first and second layers of tissue.

In some embodiments, the wound closure device is a bidirectional wound closure device.

In some embodiments, the wound closure device includes multiple first anchors that extend from the first side of each base element of the multiple base elements.

In some embodiments, the wound closure device includes multiple second anchors that extend from the second side of each base element of the multiple base elements.

In some embodiments, the repeating pattern includes a two-dimensional array.

In some embodiments, each base element of the multiple base elements has an elongate shape.

In some embodiments, the elongate shape has an aspect ratio of greater than 1:4.

In some embodiments, the repeating pattern includes a one-dimensional array of the multiple base elements arranged in a row.

In some embodiments, the first and second anchors extend substantially perpendicularly with respect to the base element.

In some embodiments, the wound closure device is configured to resist forces exerted on the first and second layers of tissue in directions parallel to a substantially planar arrangement of the multiple base elements when the first and second anchors are secured to the first and second layers of tissue.

In some embodiments, each base element of the multiple base elements includes one or more holes formed therein.

In some embodiments, the wound closure device further includes a flexible substrate to which the multiple base elements are coupled in the repeating pattern.

In some embodiments, the wound closure device is configured to hold the first and second layers of tissue against each other along the flexible substrate to close the wound.

In some embodiments, the flexible substrate includes multiple loops of material.

In some embodiments, each base element of the multiple base elements includes a hole formed therein, and a segment of the multiple loops of material passes through the hole of the base element.

In some embodiments, the hole is located along an edge of the base element.

In some embodiments, each base element of the multiple base elements includes at least two holes formed therein, and at least two segments of the multiple loops of material respectively pass through the at least two holes of the base element such that the base element couples at least two loops of the multiple loops of material to each other.

In some embodiments, loops of the multiple loops of material are interlocked with each other.

In some embodiments, the first anchor includes a shaft and a head disposed at an end of the shaft, and the first anchor has a length in a range of 5 mm to 10 mm and a head width in a range of 0.3 mm to 0.5 mm, or a length in a range of 0.75 mm to 1.25 mm and a head width in a range of 0.1 mm to 0.15 mm, or a length in a range of 0.1 mm to 0.2 mm and a head width in a range of 0.1 mm to 0.15 mm, or a length in a range of 2.75 mm to 3.25 mm and a head width in a range of 0.1 mm to 0.15 mm.

In some embodiments, the first anchor is made of a single material.

In some embodiments, the first anchor includes a central core including a first material and an outer shell including a second material that differs from the first material.

In some embodiments, the first material is harder than the second material.

In some embodiments, the first anchor includes a shaft and a head disposed at an end of the shaft, wherein the head includes a sharp tip, multiple barbs extending away from the sharp tip and radially outward from the shaft, and multiple flexible support members respectively connected to the multiple barbs and to the shaft to limit an extent to which the multiple barbs can move radially outward from the shaft.

In some embodiments, the head is configured such that during a penetration of the first anchor into the first layer of tissue in the first direction, the multiple barbs move radially inward toward the shaft, and after the penetration and during a movement of the first anchor within the first layer of tissue in the second direction, the multiple barbs are prevented from being directed toward the sharp tip.

In some embodiments, during the movement of the first anchor within the tissue in the second direction, the multiple barbs move radially outward from the shaft to secure the first anchor to the first layer of tissue.

In some embodiments, each of the multiple base elements, the first anchor, and the second anchor includes one or more polymers.

In some embodiments, the multiple base elements have a different material formulation than at least one of the first anchor and the second anchor.

In some embodiments, at least one of the multiple base elements, the first anchor, and the second anchor includes one or more of polydioxanone, polyglyconate, or polypropylene.

In some embodiments, the first and second anchors include a resorbable material.

In some embodiments, at least one of the multiple base elements, the first anchor, and the second anchor includes a material that elutes a drug.

In another aspect, an anchor of a wound closure device includes a shaft and a head disposed at an end of the shaft, wherein the head includes a sharp tip, multiple barbs extending away from the sharp tip and radially outward from the shaft, and multiple flexible support members respectively connected to the multiple barbs and to the shaft to limit an extent to which the multiple barbs can move radially outward from the shaft.

Embodiments may provide one or more of the following features.

In some embodiments, the head is configured such that during a penetration of the anchor into a tissue in a first direction, the multiple barbs move radially inward toward the shaft, and after the penetration and during a movement of the anchor within the tissue in a second direction that is opposite to the first direction, the multiple barbs are prevented from being directed toward the sharp tip.

In some embodiments, during the movement of the anchor in the second direction, the multiple barbs move radially outward from the shaft to secure the anchor to the tissue.

In some embodiments, the anchor has a length in a range of 5 mm to 10 mm and a head width in a range of 0.3 mm to 0.5 mm, or a length in a range of 0.75 mm to 1.25 mm and a head width in a range of 0.1 mm to 0.15 mm, or a length in a range of 0.1 mm to 0.2 mm and a head width in a range of 0.1 mm to 0.15 mm, or a length in a range of 2.75 mm to 3.25 mm and a head width in a range of 0.1 mm to 0.15 mm.

In some embodiments, the anchor is made of a resorbable material.

In some embodiments, the shaft and at least a portion of the head are formed from an injection molding process, and multiple barbs are formed from a subsequently performed subtraction process.

In another aspect, a method of closing a wound during a surgical procedure includes placing a wound closure device between a first layer of tissue along the wound within a body and a second layer of tissue along the wound within the body. The wound closure device includes multiple first anchors extending in a first direction toward the first layer of tissue and multiple second anchors extending in a second direction that is opposite to the first direction and toward the second layer of tissue. The method further includes causing the multiple first and second anchors to respectively penetrate the first and second layers of tissue to hold the first and second layers of tissue against each other to close the wound.

Embodiments may provide one or more of the following features.

In some embodiments, the method further includes performing the method without emplacing a drain in association with closure of the wound.

In some embodiments, the surgical procedure includes an abdominoplasty, a diastasis recti repair, a reconstructive plastic surgery, a breast reduction or reconstruction, a face-lift, a mastectomy, a muscle repair, or a hernia repair.

In some embodiments, the multiple first anchors and the multiple second anchors extend respectively from first and second sides of a substantially planar interface of the wound closure device, and causing the multiple first and second anchors to respectively penetrate the first and second layers of tissue includes closing the wound along the substantially planar interface between the first and second layers of tissue internal to the body.

In some embodiments, each anchor of the multiple first and second anchors includes a shaft and a head disposed at an end of the shaft, wherein the head includes a sharp tip and multiple barbs extending away from the sharp tip and radially outward from the shaft.

In some embodiments, causing the multiple first and second anchors to respectively penetrate the first and second layers of tissue includes moving the multiple barbs radially inward toward the shaft.

In some embodiments, after a penetration of the multiple first and second anchors, the multiple barbs are prevented from being directed toward the sharp tip.

In some embodiments, after the penetration, the multiple barbs are permitted to move radially outward from the shaft to secure the multiple first and second anchors respectively to the first and second layers of tissue.

In some embodiments, each anchor of the multiple first and second anchors further includes multiple flexible support members respectively connected to the multiple barbs and to the shaft, and the method further includes limiting an extent to which the multiple barbs can move radially outward from the shaft.

In some embodiments, the wound closure device further includes a flexible substrate, wherein the multiple first anchors extend from a first side of the flexible substrate in the first direction, and wherein the multiple second anchors extend from a second side of the flexible substrate in the second direction.

In some embodiments, the wound closure device further includes multiple base elements coupled to the flexible substrate in a repeating pattern across the flexible substrate.

In some embodiments, each first anchor of the multiple first anchors extends from a first side of one respective base element of the multiple base elements, each second anchor of the multiple second anchors extends from a second side of one respective base element of the multiple base elements, and the second side is opposite the first side.

In some embodiments, causing the multiple first and second anchors to respectively penetrate the first and second layers of tissue includes pressing the first layer of tissue onto the multiple first anchors and pressing the multiple second anchors into the second layer of tissue.

Figure 1A:
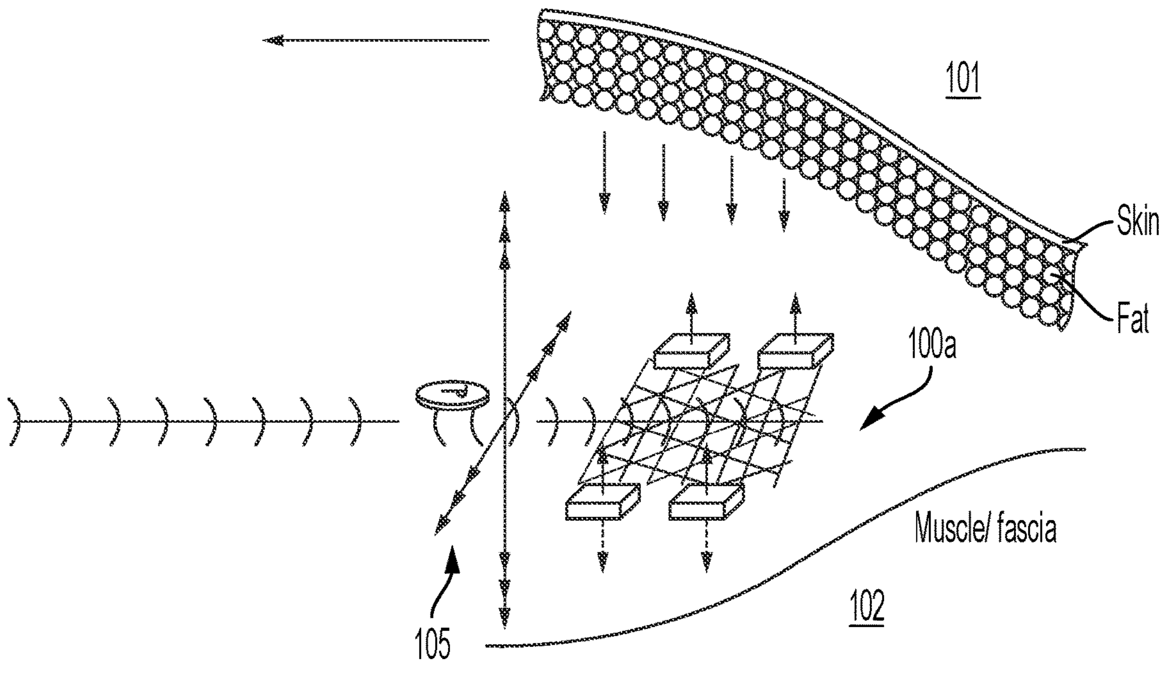
FIG. 1A illustrates a wound closure device including multiple rigid barbed elements connected via flexible elements, according to example embodiments.

Other embodiments not shown herein are contemplated.

DETAILED DESCRIPTION

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

It is desirable as part of a variety of medical procedures to secure two tissues together along a planar interface (e.g., between a skin flap and underlying muscle/fascia) in a manner that avoids seroma formation and infection, prevents dehiscence, provides support to the tissues along and across the planar interface, supplies tension to the tissues to enhance wound healing, decrease tension applied to incisions, and prevent puckering, sagging, or other unwanted tissue migration, and/or that satisfies some other aims of a medical procedure. For example, abdominoplasties, breast reductions or reconstructions, facelifts, mastectomies, hernias, or other procedures include securing neighboring tissues together across a large, planar interface.

Simply placing the tissues in an opposing manner, with sutures or other securing means emplaced along the edge(s) of the interface between the opposing tissues, often results in seroma, hematomas, or other fluid buildup between the opposing tissues, which can lead to infection. The use of sutures in this manner can also take an extended time to emplace, and can lead to puckering in the skin. Correction of these issues can require additional surgical interventions and/or higher experience on the part of the surgeon. To ameliorate these issues, drains can be emplaced, but drains require additional postoperative care and eventual removal, and do not prevent seroma formation or other fluid buildup in all circumstances. Additionally or alternatively, multiple sutures can be placed between the tissues at a variety of places across the interface between the tissues. However, this requires a great deal of time, effort, and skill on the part of the surgeon and can still lead to puckering, seroma formation, or other unwanted effects (e.g., due to the lack of support in directions parallel to the interface between the tissues, due to imperfections in the placement of the sutures, or other factors). Such procedures can also increase the time a patient is in the operating theater and/or under anesthesia, with concomitant increased risks inter alia of infection or other deleterious sequelae.

Wound closure devices and systems described herein (which can be referred to as "scaffolds") provide improved outcomes with regard to healing, cosmesis, post-operative care, and other metrics of interest. These systems include a flexible mesh or other substrate (e.g., a woven material, a set of loops of material interlocking with each other) in which is embedded multiple anchoring elements. Each anchoring element includes a base element, via which the anchoring element is coupled to the flexible substrate, and one or more anchors extending from the base element that can penetrate into tissue and then, using barbs or other means, become fixed in the tissue. Where the anchors extend in both directions from the base elements, they can provide 'vertical' support between two neighboring volumes of tissue. The connection, via the base elements, to the flexible substrate also allows the wound closure device to provide support in one or both directions parallel to the plane of the interface between the tissues. Further, where the flexible substrate is porous, composed of multiple loops or open elements, or otherwise configured to permit or enhance ingrowth of tissue, the flexible substrate can provide enhanced support over time as tissue ingrowth proceeds.

Note that, while reference is made to an interface 'between' two volumes of tissue, the wound closure devices described herein can be applied to provide support along the 'external interface' between skin or some other exposed tissue and the environment of the body. This can be done, e.g., to provide tension along the surface of the skin or other tissue and to transmit that tension across one or more incisions in the tissue, to transmit that tension across a wider area of the tissue (e.g., to areas of the tissue whose interface with underlying tissues has not been recently surgically interrupted), or to transmit tension in some other manner to facilitate healing, reduce sagging, puckering, or loosening of the tissue, to improve cosmetic outcomes, or to provide some other benefit.

The clinical benefits of the devices described herein include, but are not limited to: 1) providing tension relief on internal suture-based repairs to allow a longer time for fibrosis and scar healing of the suture tension line. This benefit can be applied to any suture line under tension or that might exhibit poor wound healing due to other conditions, e.g., hernia repairs, muscle repairs, incisions under tension or with poorly vascularized tissue due to e.g., smoking, radiation or other conditions. 2) Reducing or completely preventing 'dead space' between the fascia/muscle and subcutaneous interspace (or some other inter-tissue interface) which can limit to formation of seroma or low pressure hematoma/bleeding, thereby reducing infections or chronic seromas and the need for postoperative drains. 3) Reducing the intraoperative time, effort, and skill to close incisions, under tension or not, via transcutaneous application as well as when used to effect subcutaneous/intermediate layer closure using a bidirectional scaffold placed in a perpendicular direction to approximate the subcutaneous and deep dermal layers of tissue.

A scaffold as described herein can include a flexible substrate composed of interlocking loops of polymer (or other material) and solid platforms (which can also be referred to as "base elements") of polymer (or other material) which have holes or other features to facilitate mechanical connection with the loops of the flexible substrate. The loops and platforms can be arranged along horizontal and vertical directions with a repeating pattern of multiple loops followed by a platform. The platforms can be manufactured separately with a directional anchor (which can include one or more spurs/barbs) that permits one way movement into tissue but that resists movement in the opposite direction, thereby allowing the directional anchors to be inserted into tissue so as to anchor the platforms, and by extension the flexible substrate, to multiple locations along a surface of the tissue(s).

The spurs or barbs of each anchor can be similar to a porcupine quill or a grappling hook with the ability to penetrate and move in one direction into tissue but to resist movement in the opposite direction out of the tissue. This directional preference allows for stabilization of the scaffold/flexible substrate as well as the approximation and fixture of the different layers of the tissue(s). The loops of the flexible substrate in the horizontal and vertical directions can be manufactured to resist stretching and pulling along the plane parallel to the plane of the flexible substrate. The anchors of the platforms couple such resistive parallel forces into the tissue(s) while also resisting movement in the direction perpendicular to the flexible substrate (e.g., resisting forces that can separate opposing tissues, resulting in dehiscence or other unwanted effects).

FIG. 1A depicts the use of an example scaffold 100*a* as described herein to provide support across and along an interface between two tissues. The scaffold 100*a* has been placed between an overlying flap of tissue 101 (in the depicted example, fat and skin of a flap created as part of a diastasis recti repair procedure) and underlying tissue 102 (in the depicted example, muscle and fascia of the abdomen, e.g., rectus abdominus and other near-midline abdominal muscles and associated tissue). The overlying tissue 101 can then be pressed down onto the underlying tissue 102, causing anchors (e.g., barbs) of the scaffold 100*a* to become anchored into both the tissues 101, 102. The anchors are mechanically coupled to each other indirectly via a flexible substrate, which couples together base elements to which the anchors are directly coupled. The scaffold 100*a*, once implanted in this manner, provides support across and along the interface between the tissues 101, 102 (the direction of these supportive forces is indicated by the arrows 105 in FIG. 1A). These supporting forces include forces perpendicular to the plane of the tissue interface (e.g., to keep the two layers of tissue together, to prevent seroma formation and/or dehiscence, to promote fascia regrowth across the interface) as well as forces parallel to the plane of the tissue interface (e.g., to provide support along the interface to enhance tissue healing, to provide distributed support across a diastasis or other incision or tear in one or both of the tissues 101, 102, etc.). The use of the scaffold 100*a* allows such support to be provided evenly, and with reduced surgical time and expertise (e.g., relative to the manual placement of an array of individual sutures across the tissue interface).

Figure 1B:
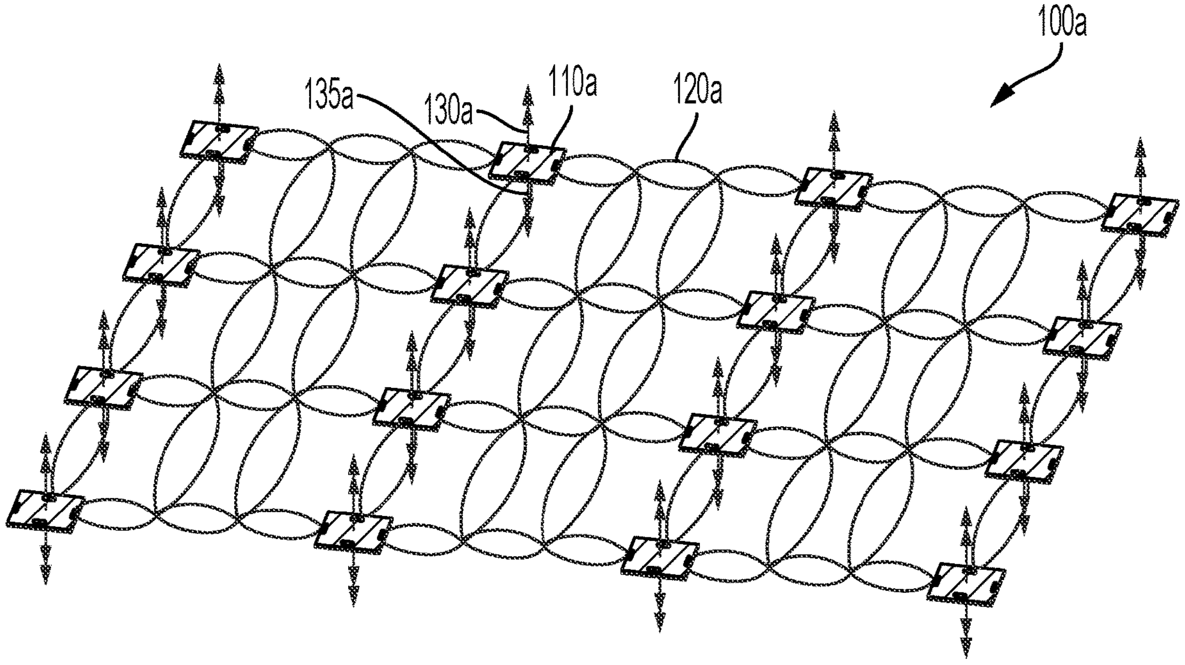
FIG. 1B illustrates a wound closure device including multiple rigid barbed elements connected via flexible elements, according to example embodiments.

FIG. 1B depicts elements of the example scaffold 100*a* as described herein. The scaffold 100*a* includes a number of base elements (including example base element 110*a*) arranged in a repeating two-dimensional array and embedded in a flexible substrate that is composed of multiple interlinked loops of material (include example loop 120*a*). Each base element includes a first anchor (including example anchor 130*a*) directed in a first direction ('up' in FIG. 1B) relative to the flexible substrate and a second anchor (including example anchor 135*a*) directed in a second direction ('down' in FIG. 1B), opposite the first direction, relative to the flexible substrate.

The scaffold of FIG. 1B can be referred to as a "bidirectional" scaffold, as it includes anchors directed in both directions relative to the flexible substrate of the scaffold. However, in some applications (e.g., application of a scaffold to an external surface of skin, application of a scaffold on an internal surface of peritoneum or some other internal tissue surface that must move freely relative to underlying tissues), it is beneficial to provide anchors in only one direction relative to the flexible substrate of the scaffold.

Figure 1C:
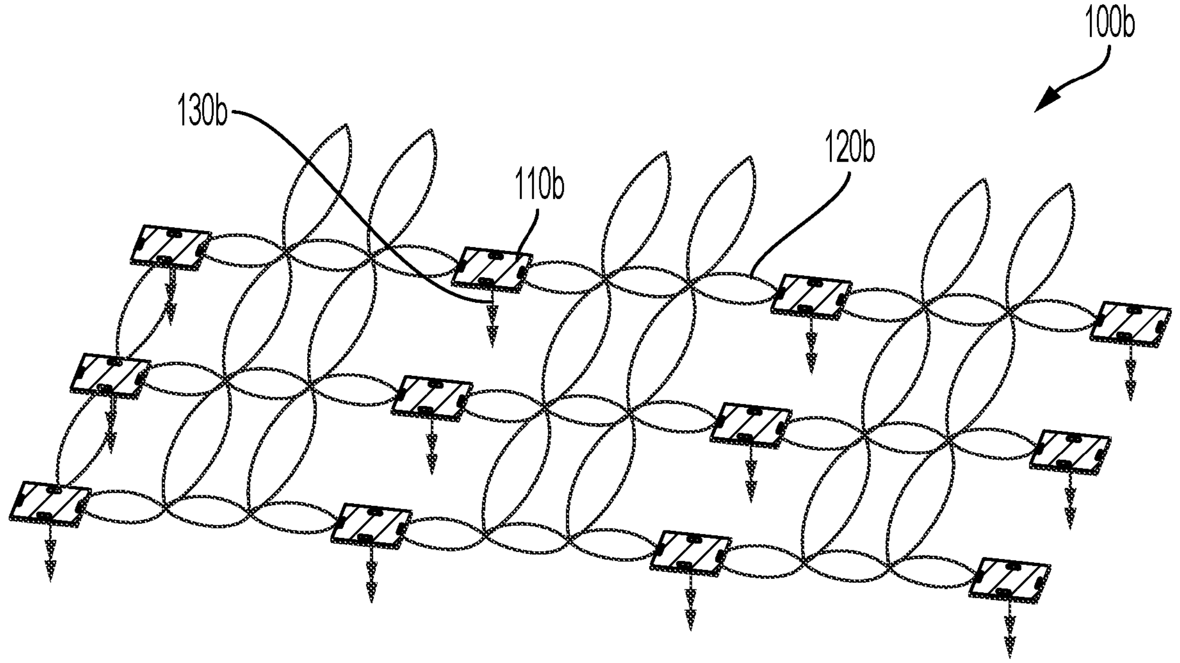
FIG. 1C illustrates a wound closure device including multiple rigid barbed elements connected via flexible elements, according to example embodiments.

FIG. 1C depicts elements of such a "unidirectional" scaffold 100*b*. The scaffold 100*b* includes a number of base elements (including example base element 110*b*) arranged in a repeating two-dimensional array and embedding in a flexible substrate that is composed of multiple interlinked loops of material (include example loop 120*b*). Each base element includes an anchor (including example anchor 130*b*) directed in the same direction ('down' in FIG. 1C) relative to the flexible substrate.

Figure 1D:
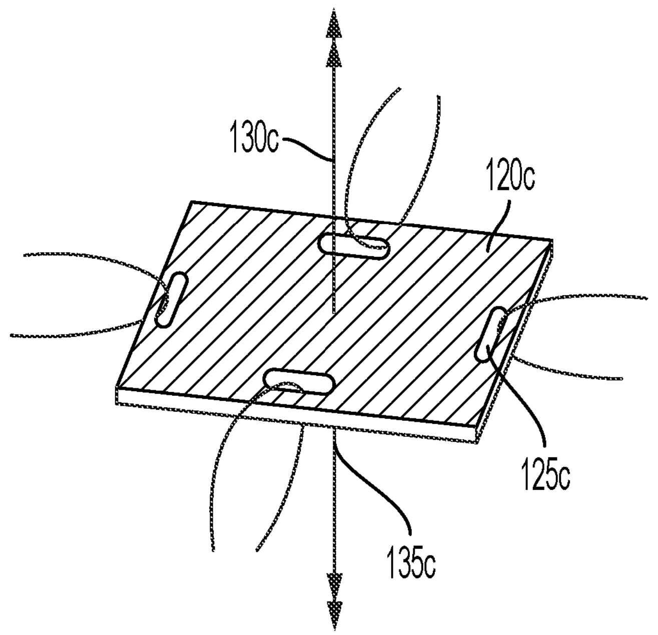
FIG. 1D illustrates a rigid barbed element of a wound closure device, according to example embodiments.

FIG. 1D depicts an example base element 120*c* of a scaffold and elements of the scaffold related thereto. First 130*c* and second 135*c* anchors are rigidly coupled to the base element 120*c*. These anchors can be fabricated separately (e.g., by an injection-molding process) from the base element 120*c* and later coupled thereto (e.g., using adhesives, laser welding, press fitting, tabs or other locking features) or can be formed as a single continuous element with the base element 120*c* (e.g., via an injection molding process). The base element 120*c* includes a number of holes (including example hole 125*c*) through which loops or other elements of a flexible substrate of the scaffold can be passed in order to couple mechanically couple the base element 120*c* (and the anchors 130*c*, 135*c* coupled thereto) to the flexible substrate of the scaffold. However, alternative means for effecting such coupling can be employed (e.g., adhesives, using heat to melt portions of the base element 120*c* around or through loops, fabric, or other element(s) of the flexible substrate or vice-versa). The base element 120*c* provides a means for mechanically coupling the flexible substrate of a scaffold to the anchors of the scaffold, and thus to tissue(s) to which the anchors can be fixed intraoperatively. The base element 120*c* can also provide means for manipulating and inserting the anchors, means for easing the manufacturing of the scaffold, or other benefits.

Note that, while the flexible substrate of the scaffolds depicted in FIGS. 1B-D are depicted as sets of interlinked loops of flexible material, alternative configurations of flexible substrate are possible. The flexible substrate can include woven or knitted materials, sheets of material (e.g., with slits, holes, or other features cut or otherwise formed therethrough), interlocking rigid elements (e.g., chain links, bars coupled by hinges), or other materials, elements, or combinations thereof. The flexible substrate can also include knots, ripstops, weaves, or other features to allow the flexible substrate to be cut or otherwise sized to an application intraoperatively (e.g., to match a commercially-available size of scaffold to the actual size and shape of a patient's tissue(s)) without resulting in the unraveling of the substrate or some other manner of dissolution or disintegration of the flexible substrate.

The materials of the flexible substrate, base elements, and/or anchors can be resorbable, non-resorbable, configured to elute a drug (e.g., an antibiotic to prevent infection, some other drug to promote wound healing), or composed of some material or combination of materials according to an application. Such materials can include polydioxanone, polyglyconate, or polypropylene. The materials will primary be polydioxanone and possible polyglyconate although polypropylene will possibly be an option if permanent material is needed. For example, the base elements and anchor can be made of resorbable materials (e.g., polydioxanone, polyglyconate) while the flexible substrate is composed of a non-resorbable material (e.g., polypropylene) such that the flexible substrate remains in the body following wound healing, so as to provide support to tissues that have grown through it. Alternatively, the rate of resorption of different elements of the scaffold can be tailored (e.g., by adjusting a ratio of a copolymer, by adjusting a degree of branching or mean length of a polymer) according to an application. For example, all of the elements of the scaffold can be composed of resorbable materials (e.g., polydioxanone), but their rates of resorbtion can be specified such that the anchors resorb quickly (e.g., to improve comfort once the initial period of wound healing has occurred, thus reducing the need for fixation provided by the anchors) while the flexible substrate resorbs more slowly (to provide parallel tension support to tissues that have grown through the material of the flexible substrate). For example, antibiotic impregnated polymer can be employed as well as possible slow release drugs that can be added to a transcutaneous unidirectional scaffold or to a subcutaneous scaffold to prevent or reduce infection and/or scarring.

As shown in FIGS. 1B-C, each base element of a scaffold as described herein can include no more than a single anchor per direction, and the base element itself can have a relatively 'compact' shape (e.g., a circular, square, or other shape having an aspect ratio of near 1:1). However, in some examples, it can be beneficial to provide base elements with more than one anchor per direction and/or having elongate shapes. Such "strut"-type base elements can provide additional stiffening in all directions, and in both tension and compression, across their area. This configuration can provide forces to counter compression parallel to the plane of the scaffold, which the flexible substrate of the scaffold cannot do (the flexible substrate can provide forces to resist tension parallel to the scaffold, but, being flexible, is likely to buckle under compression).

Figure 2A:
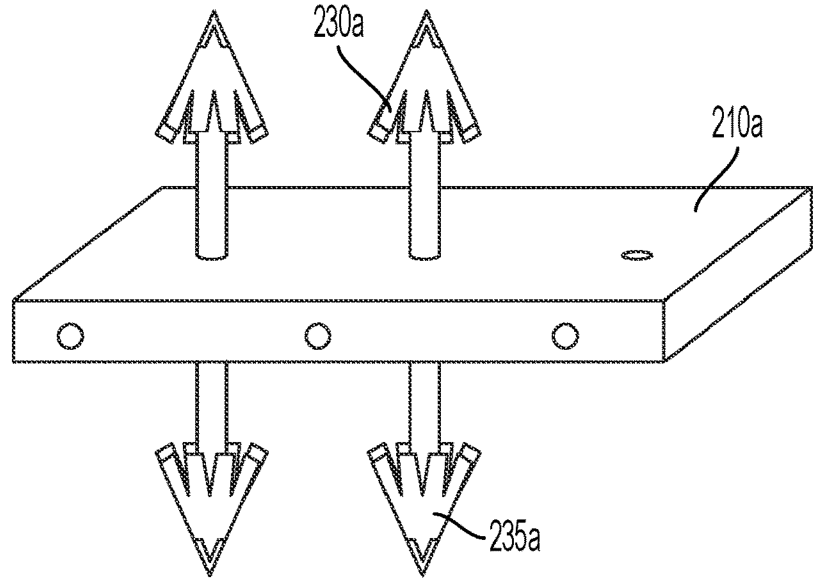
FIG. 2A illustrates a rigid barbed element of a wound closure device, according to example embodiments.
Figure 2B:
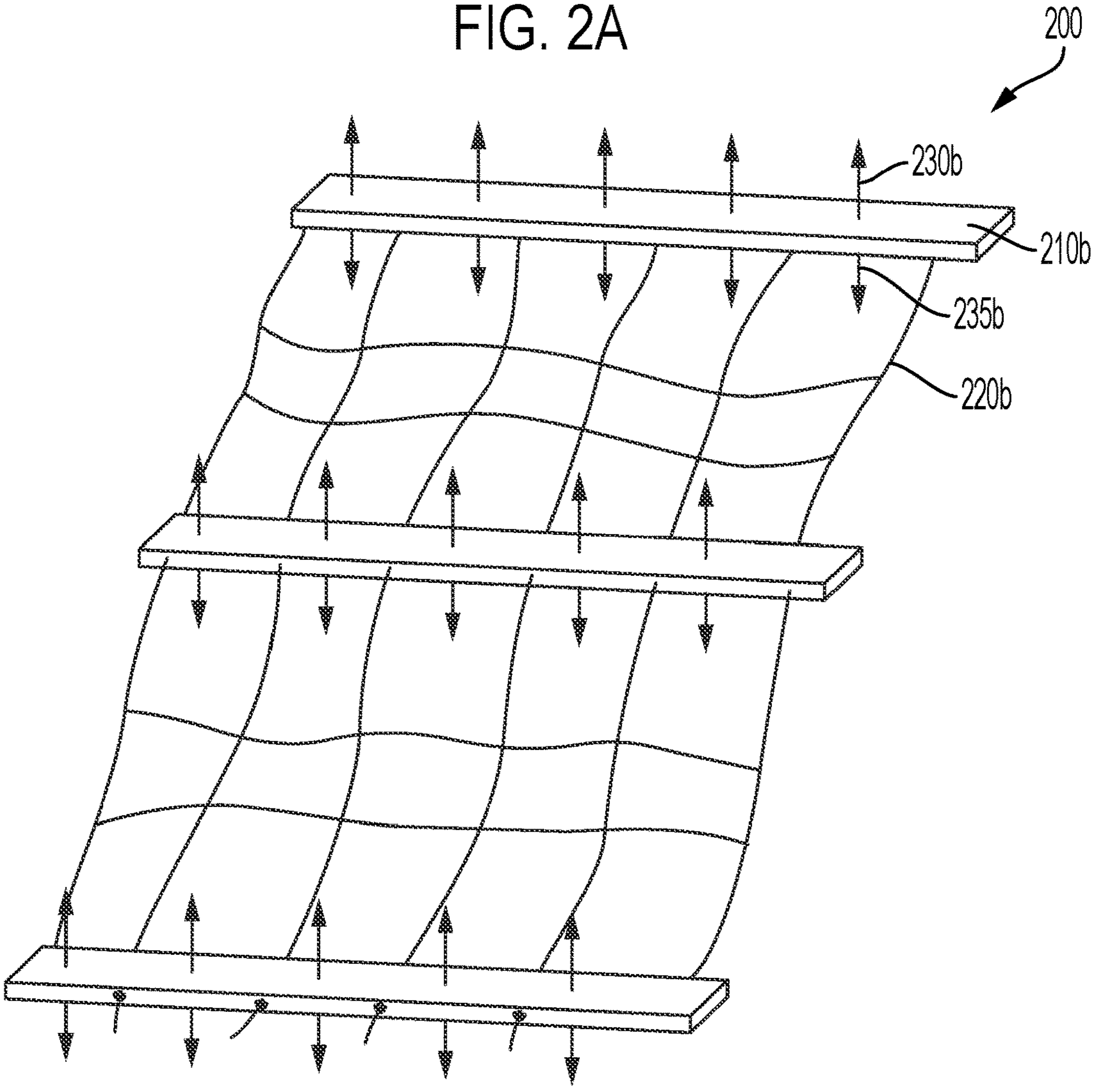
FIG. 2B illustrates a wound closure device including multiple rigid barbed elements connected via flexible elements, according to example embodiments.

FIG. 2A depicts an example "strut-type" base element 210*a* of a scaffold and elements of the scaffold related thereto. A first set of anchors (including example first anchor 230*a*) and a second set of anchors (including example second anchor 235*a*) are rigidly coupled to the base element 210*a* and directed in opposite directions, respectively, from a plane of the base element 210*a*/scaffold. Such a strut-type base element can have an elongate aspect ratio, e.g., an aspect ratio greater than 1:4, to allow the base element to resist forces in all directions along an elongate area or length. FIG. 2B depicts elements of a scaffold 200 that includes a number of such strut-type base elements (including example base element 210*b*) arranged in a repeating one-dimensional array and embedded in a flexible substrate 220*b*. Each base element includes a first set of anchors (including example anchor 230*b*) directed in a first direction ('up' in FIG. 2B) relative to the flexible substrate and a second set of anchors (including example anchor 235*b*) directed in a second direction ('down' in FIG. 2B) relative to the flexible substrate and opposite the first direction.

The anchors of a scaffold, which include a central 'shaft' that terminates in a 'head,' can be configured in a variety of ways and have dimensions specified according to a target tissue type (e.g., skin of the face, skin of the body, subcutaneous skin and underlying muscle/fascia). The shaft mechanically couples the head to a base element. The head includes multiple spurs, barbs, or other features to facilitate insertion into and fixation in target tissue.

In examples where the scaffold is employed unidirectionally on the external surface of skin (e.g., skin of the face), the anchor length can range from 50 to 200 um to allow for less pain on insertion as well as lowering the risk of scarring in the papillary dermis. The size of the scaffold will also vary depending on location. The anchor can have a head width between 0.3 mm and 0.5 mm and a length between 5 mm and 10 mm for use in internal fixation between volumes of tissue (e.g., between skin of the body and underlying muscle/ fascia). The anchor can have a head width between 0.1 mm and 0.15 mm and a length between 0.75 mm and 1.25 mm and/or a length between 0.1 mm and 0.2 mm for applications involving skin of the face. The anchor can have a head width between 0.1 mm and 0.15 mm and a length between 2.75 mm and 3.25 mm for applications involving subcutaneous fixation of skin of the face.

Figure 3A:
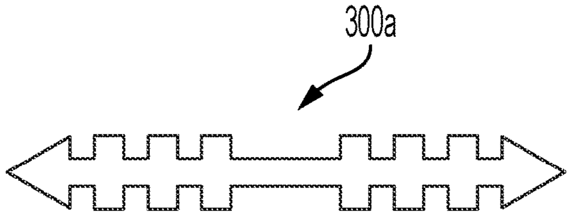
FIG. 3A illustrates a barbed element of a wound closure device, according to example embodiments.
Figure 3B:
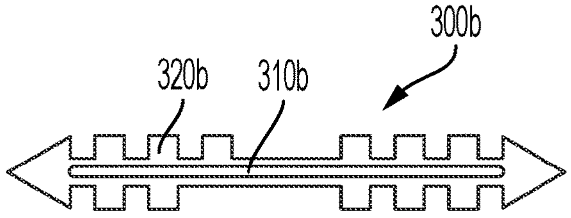
FIG. 3B illustrates a barbed element of a wound closure device, according to example embodiments.

The anchors can be composed of multiple different materials to tailor the resistance or resorption profile, to facilitate manufacturing or insertion into tissue, or to provide some other benefit. FIG. 3A shows an example bidirectional anchor 300*a* composed of a single material throughout. FIG. 3B shows an example bidirectional anchor 300*b* having a core 310*b* composed of a first material (e.g., a harder and/or stiffer material, a material that softens when exposed to fluid to allow for resilience to facilitate initial insertion followed by softness for enhanced comfort) surrounded by a shell 320*b* composed of a second material that differs from the first material (e.g., a softer material to facilitate the action of barbs formed therein, a drug-eluting material). The difference in materials can facilitate sharpening the center of the anchor and/or maintaining the sharpness of the anchor while allowing barbs or other features formed in the shell to have the proper compliance to 'flatten' against the center of the anchor during penetration and then rebound to become fixed within tissue.

Figure 4:
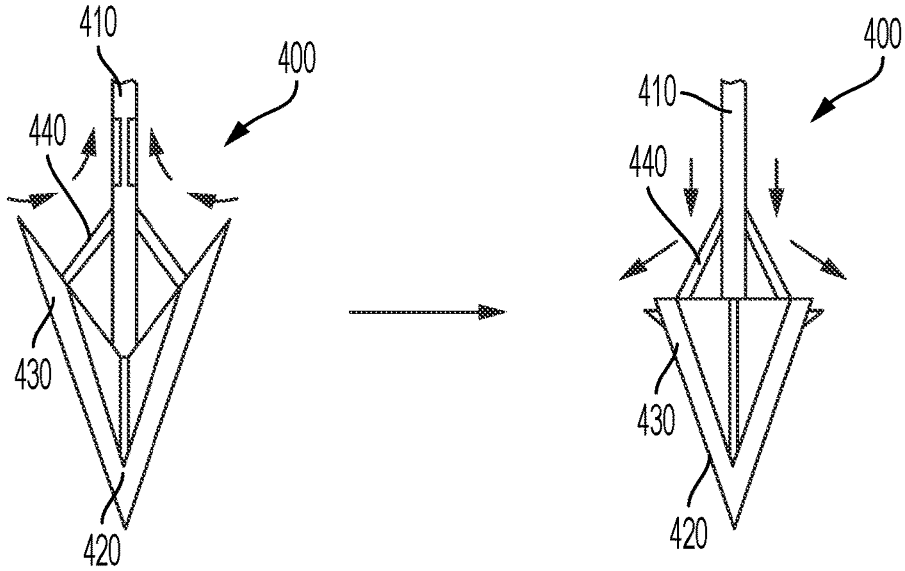
FIG. 4 illustrates a barbed element of a wound closure device, according to example embodiments.

FIG. 4 illustrates aspects of such an insertion process for an example anchor 400. The anchor 400 includes a head attached to a shaft 410. The head includes a sharp tip 420 and a number of barbs 430 directed away from the shaft 410 and in a direction opposite the tip 420. The left pane of FIG. 4 depicts the initial insertion of the anchor 400, during which forces from the tissue being penetrated result in the barbs 430 being compressed against the shaft 410 (motions/forces indicated by the arrows). The right pane of FIG. 4 depicts, subsequent to insertion, partial retraction of the anchor 400 results in the barbs 430 being drawn outward, away from the shaft 410, thereby fixing the anchor 400 in place in the tissue (motions/forces indicated by the arrows).

As shown in FIG. 4, an anchor can include a number of flexible supports 440, each flexible support 440 coupling an end portion of a respective barb 430 to the shaft 410 of the anchor 400 such that the flexible supports 440 prevent the barbs 430 from being directed toward the tip 420 of the anchor 400 as a result of retraction of the anchor 400 subsequent to penetration of the anchor 400 into the tissue.

An anchor as described herein can be fabricated via a variety of methods. In some examples, the anchor can be formed using injection molding or other techniques to provide the bulk of the material of the anchor. In some example, additional subtractive processes (e.g., laser or mechanical cutting to remove volumes of the anchor material, laser ablation) can be applied to form the barbs or other features of the anchor. This can be done to form geometries that are difficult or impossible to achieve via injection molding or other techniques used to provide initial forming of the anchor, to avoid pre-straining or pre-stressing the barbs as they come out of a mold, to provide for sharper features, to remove material internal to the barbs to allow the barbs to deform more toward the shaft during insertion, or to provide some other benefit.

Figure 5:
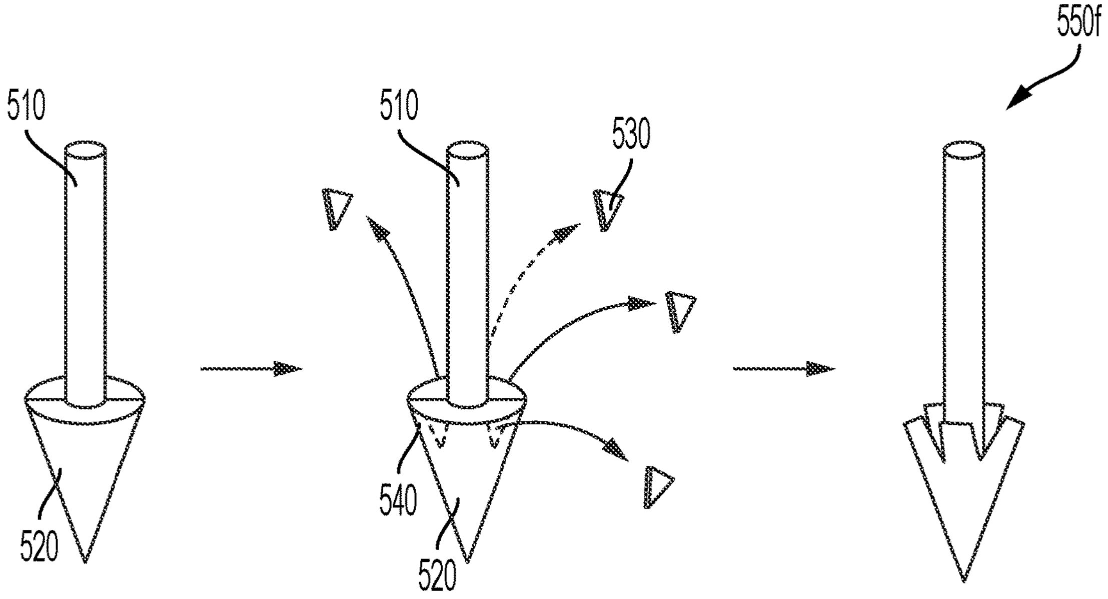
FIG. 5 illustrates aspects of the manufacture of a rigid barbed element of a wound closure device, according to example embodiments.

FIG. 5 depicts steps of an example method for forming an anchor as described herein. An initial step of the method, depicted in the left panel of FIG. 5, includes providing (e.g., by injection molding) a shaft 510 of the anchor that terminates in a sharp point 520 capable of penetrating tissue. The center pane of FIG. 5 depicts a subsequent step of the method, wherein two or more volumes of material (including example cut volume 530) from the shaft 510 of the anchor, thereby forming two or more barbs (including example barb 540) that are directed outward from the shaft 510 and away from the sharp point 520 of the anchor such that penetration of the sharp 520 point of the anchor into tissue causes deformation of the barbs 540 toward the center of the shaft 510 and further such that retraction of the anchor subsequent to penetration of the sharp point 520 of the anchor into the tissue causes the barbs 540 to expand outward from the shaft, thereby anchoring the anchor in the tissue. The right pane of FIG. 5 depicts to completed anchor 550.

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

I claim:

1. A wound closure device comprising:
- a plurality of base elements arranged in a repeating pattern;
- a first anchor extending from a first side of each base element of the plurality of base elements in a first direction for securing itself to a first layer of tissue along a wound within a body; and
- a second anchor extending from a second side of each base element of the plurality of base elements in a second direction that is opposite to the first direction for securing itself within a second layer of tissue along the wound, such that the wound closure device is configured to hold the first and second layers of tissue against each other to close the wound, wherein the first anchor comprises:
- a shaft, and
- a head disposed at an end of the shaft, the head comprising:
  - a sharp tip,
  - a plurality of barbs extending away from the sharp tip and radially outward from the shaft, and
  - a plurality of flexible support members respectively connected to the plurality of barbs and to the shaft to limit an extent to which the plurality of barbs can move radially outward from the shaft.

2. The wound closure device of claim 1, wherein the wound closure device is configured to be disposed internal to the body between the first and second layers of tissue.

3. The wound closure device of claim 2, wherein the wound closure device comprises a bidirectional wound closure device.

4. The wound closure device of claim 1, wherein the wound closure device comprises a plurality of first anchors that extend from the first side of each base element of the plurality of base elements.

5. The wound closure device of claim 4, wherein the wound closure device comprises a plurality of second anchors that extend from the second side of each base element of the plurality of base elements.

6. The wound closure device of claim 1, wherein the repeating pattern comprises a two-dimensional array.

7. The wound closure device of claim 1, wherein each base element of the plurality of base elements has an elongate shape.

8. The wound closure device of claim 7, wherein the elongate shape has an aspect ratio of greater than 1:4.

9. The wound closure device of claim 7, wherein the repeating pattern comprises a one-dimensional array of the plurality of base elements arranged in a row.

10. The wound closure device of claim 1, wherein the first and second anchors extend substantially perpendicularly with respect to the base element.

11. The wound closure device of claim 1, wherein the wound closure device is configured to resist forces exerted on the first and second layers of tissue in directions parallel to a substantially planar arrangement of the plurality of base elements when the first and second anchors are secured to the first and second layers of tissue.

12. The wound closure device of claim 1, wherein each base element of the plurality of base elements includes one or more holes formed therein.

13. The wound closure device of claim 1, further comprising a flexible substrate to which the plurality of base elements are coupled in the repeating pattern.

14. The wound closure device of claim 13, wherein the wound closure device is configured to hold the first and second layers of tissue against each other along the flexible substrate to close the wound.

15. The wound closure device of claim 13, wherein the flexible substrate comprises a plurality of loops of material.

16. The wound closure device of claim 15, wherein each base element of the plurality of base elements includes a hole formed therein, and wherein a segment of the plurality of loops of material passes through the hole of the base element.

17. The wound closure device of claim 16, wherein the hole is located along an edge of the base element.

18. The wound closure device of claim 15, wherein each base element of the plurality of base elements includes at least two holes formed therein, and wherein at least two segments of the plurality of loops of material respectively pass through the at least two holes of the base element such that the base element couples at least two loops of the plurality of loops of material to each other.

19. The wound closure device of claim 15, wherein loops of the plurality of loops of material are interlocked with each other.

20. The wound closure device of claim 1, wherein the first anchor comprises a shaft and a head disposed at an end of the shaft, and wherein the first anchor has:

a length in a range of 5 mm to 10 mm and a head width in a range of 0.3 mm to 0.5 mm; or a length in a range of 0.75 mm to 1.25 mm and a head width in a range of 0.1 mm to 0.15 mm; or a length in a range of 0.1 mm to 0.2 mm and a head width in a range of 0.1 mm to 0.15 mm; or a length in a range of 2.75 mm to 3.25 mm and a head width in a range of 0.1 mm to 0.15 mm.

21. The wound closure device of claim 1, wherein the first anchor is made of a single material.

22. The wound closure device of claim 1, wherein the first anchor comprises a central core comprising a first material and an outer shell comprising a second material that differs from the first material.

23. The wound closure device of claim 22, wherein the first material is harder than the second material.

24. The wound closure device of claim 1, wherein the head is configured such that:

during a penetration of the first anchor into the first layer of tissue in the first direction, the plurality of barbs moves radially inward toward the shaft, and after the penetration and during a movement of the first anchor within the first layer of tissue in the second direction, the plurality of barbs is prevented from being directed toward the sharp tip.

25. The wound closure device of claim 24, wherein during the movement of the first anchor within the tissue in the second direction, the plurality of barbs moves radially outward from the shaft to secure the first anchor to the first layer of tissue.

26. The wound closure device of claim 1, wherein each of the plurality of base elements, the first anchor, and the second anchor comprises one or more polymers.

27. The wound closure device of claim 26, wherein the plurality of base elements has a different material formulation than at least one of the first anchor and the second anchor.

28. The wound closure device of claim 26, wherein at least one of the plurality of base elements, the first anchor, and the second anchor comprises one or more of polydioxanone, polyglyconate, or polypropylene.

29. The wound closure device of claim 1, wherein the first and second anchors comprise a resorbable material.

30. The wound closure device of claim 1, wherein at least one of the plurality of base elements, the first anchor, and the second anchor comprises a material that elutes a drug.

31. A wound closure device comprising:

a plurality of base elements arranged in a repeating pattern;

a first anchor extending from a first side of each base element of the plurality of base elements in a first direction for securing itself to a first layer of tissue along a wound within a body;

a second anchor extending from a second side of each base element of the plurality of base elements in a second direction that is opposite to the first direction for securing itself within a second layer of tissue along the wound, such that the wound closure device is configured to hold the first and second layers of tissue against each other to close the wound; and a flexible substrate to which the plurality of base elements are coupled in the repeating pattern, wherein the flexible substrate comprises a plurality of loops of material, wherein each base element of the plurality of base elements includes at least two holes formed therein, and wherein at least two loops of the plurality of loops of material each pass through a respective hole of the at least two holes of at least one base element of the plurality of base elements such that the at least one base element couples the at least two loops of the plurality of loops of material to each other.

* * * * *